United States Patent
Koschinsky et al.

(10) Patent No.: US 8,024,033 B2
(45) Date of Patent: Sep. 20, 2011

(54) IONTOPHORETIC ELECTRODE

(75) Inventors: Ralph Koschinsky, Sandy, UT (US); James D. Isaacson, Salt Lake City, UT (US); Robert F. Hause, Jr., Bountiful, UT (US)

(73) Assignee: Encore Medical Asset Corporation, Henderson, NV (US)

( * ) Notice: Subject to any disclaimer, the term of this patent is extended or adjusted under 35 U.S.C. 154(b) by 1046 days.

(21) Appl. No.: 10/587,429

(22) PCT Filed: Feb. 28, 2005

(86) PCT No.: PCT/US2005/006437
§ 371 (c)(1),
(2), (4) Date: Apr. 23, 2007

(87) PCT Pub. No.: WO2005/084275
PCT Pub. Date: Sep. 15, 2005

(65) Prior Publication Data
US 2008/0058698 A1    Mar. 6, 2008

Related U.S. Application Data

(60) Provisional application No. 60/521,148, filed on Feb. 27, 2004.

(51) Int. Cl.
*A61N 1/30* (2006.01)

(52) U.S. Cl. .......................................................... 604/20
(58) Field of Classification Search ............ 604/19–22; 606/13, 14, 27, 31, 32, 41, 48, 129
See application file for complete search history.

(56) References Cited

U.S. PATENT DOCUMENTS

| | | | |
|---|---|---|---|
| 4,456,012 A | | 6/1984 | Lattin |
| 5,019,034 A | | 5/1991 | Weaver et al. |
| 5,255,692 A | * | 10/1993 | Neubauer et al. ............ 607/122 |
| 5,415,629 A | * | 5/1995 | Henley ............................ 604/20 |
| 6,615,078 B1 | * | 9/2003 | Burson et al. ................... 604/20 |
| 2002/0035345 A1 | * | 3/2002 | Beck ................................ 604/20 |

OTHER PUBLICATIONS

Supplementary European Search Report dated Jun. 7, 2010 in European Patent Office Application No. 05724060.8-2305.

* cited by examiner

*Primary Examiner* — Manuel A Mendez
(74) *Attorney, Agent, or Firm* — Ropes & Gray LLP

(57) ABSTRACT

An electrode for an iontophoretic drug delivery system includes a retainer having a malleable characteristic. The retainer and a conductor are connected to a platform. The conductor and a dose controller are electrically coupled to the iontophoretic drug delivery system. A drug delivery matrix is operably connected to the platform and proximate the conductor wherein the conductor, the drug delivery matrix, and the dose controller cooperate to deliver a drug to a user when the electrode is affixed to the user and operably connected to the iontophoretic drug delivery system.

48 Claims, 2 Drawing Sheets

IONTOPHORETIC ELECTRODE

RELATED APPLICATIONS

This application is a national phase application under 35 U.S.C. §371 of International Application Number PCT/US05/06437 filed Feb. 28, 2005, which claims priority to U.S. Provisional Patent Application No. 60/521,148, filed Feb. 27, 2004, and is incorporated by reference herein.

BACKGROUND OF THE INVENTION

1. Field of the Invention

The present invention generally relates to an iontophoretic system for delivering a medicament to an individual. More specifically, this invention relates to utilizing an iontophoretic electrode including a malleable structure or material that enables the electrode to bend or mold into a specific shape and conform to a variety of body contours. In addition, the electrode includes a means for balancing distribution of an electrical characteristic, e.g., voltage, current, or resistance, throughout the electrode for delivery of the medicament to the area to be treated.

2. Background Art

Iontophoresis is an electro-chemical process utilized to apply medication locally to and through a patient's skin. The iontophoretic technique involves applying an electrical force proximate the medicament and the area to be treated to drive ionized compounds of the medicament into the skin. Because the iontophoretic delivery technique is a non-invasive means for administering drugs to a patient, the process reduces or eliminates the adverse effects commonly associated with injecting medicaments into a patient's skin, e.g., pain, infection, and skin deformation.

Using iontophoresis to deliver a proper dose of medicament to an individual involves managing the physical and electrical characteristics of the area to be treated. Some issues include placement of the iontophoretic delivery system's electrode on the treated area, the range of skin/tissue resistance associated with the treated area, and the range of skin/tissue resistance between treated individuals. Because these physical and electrical concerns may affect iontophoretic drug delivery, the physical and electrical characteristics of the area to be treated should be considered to ensure delivery of the appropriate drug dosage. The present invention is designed to abate these and other concerns.

SUMMARY OF THE INVENTION

The present invention is directed to an electrode for an iontophoretic drug delivery system. The electrode comprises a retainer including a malleable/bendable characteristic. The retainer is operably connected to a platform. A conductor is also operably connected to the platform, as well as being electrically coupled to the iontophoretic drug delivery system. A dose controller is operably coupled to the conductor and the iontophoretic drug delivery system. A drug delivery matrix is operably connected to the platform and proximate to the conductor wherein the conductor, the drug delivery matrix, and the dose controller cooperate to deliver a drug to a user when the electrode is affixed to the user and operably connected to the iontophoretic drug delivery system.

Another aspect of the present invention involves an electrode for an iontophoretic drug delivery system comprising a conductor including a malleable/bendable characteristic. The conductor is operably connected to the platform and electrically coupled to the iontophoretic drug delivery system. A drug delivery matrix is operably connected to the platform and proximate to the conductor wherein the conductor and the drug delivery matrix cooperate to deliver a drug to a user when the electrode is affixed to the user and operably connected to the iontophoretic drug delivery system.

A further aspect of the present invention includes an electrode for an iontophoretic drug delivery system comprising a platform having at least one drug delivery area. A drug delivery matrix is operably attached to the platform and proximate the drug delivery area(s). A pair of conductors includes an active conductor electrically coupled to the iontophoretic drug delivery system; and, a dispersive (return) conductor being electrically coupled to the iontophoretic drug delivery system, wherein at least one of the pair of conductors includes a malleable/bendable characteristic. A dose controller is operably coupled to the pair of conductors wherein the pair of conductors, the drug delivery matrix, and the dose controller cooperate to deliver a drug to a user when the electrode is affixed to the user and operably connected to the iontophoretic drug delivery system.

Still additional aspects of the present invention include: a platform segmented into a plurality of drug delivery areas; an adhesive operably attached to the platform wherein the adhesive facilitates releasably securing the electrode to the user; a connector operably attached to the platform and electrically coupled to the iontophoretic drug delivery system; and a dose controller including a monitor, sensor, and electrical characteristic adjustor.

An object of the present invention is to provide a drug delivery system capable of addressing the effects related to variations in skin and/or tissue resistance associated with the area to be treated.

Another object of the present invention is to provide an electrode for a drug delivery system capable of being adhered to a variety of body contours.

Other advantages and aspects of the present invention will become apparent upon reading the following description of the drawings and detailed description of the invention.

DETAILED DESCRIPTION OF THE INVENTION

Figure 1:
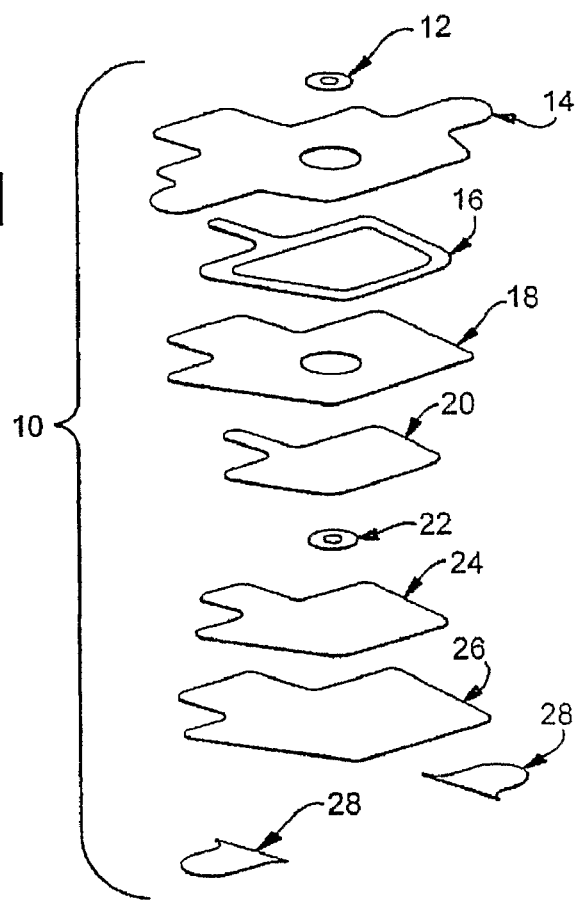
FIG. 1 is an exploded perspective view of one embodiment of an electrode of the present invention.

While the present invention is capable of embodiment in many different forms, there is shown in the drawings and will herein be described in detail several preferred embodiments of the invention with the understanding that the present disclosure is to be considered as an exemplification of the principles of the invention and is not intended to limit the broad aspect of the invention to the embodiments illustrated.

One preferred embodiment of the present invention disclosed herein includes a structural assembly wherein the assembly combines the use of an iontophoretic electrode integral with a pliable (malleable/bendable) retainer to enable the electrode to be bent, molded, and retained into a specific shape to conform to a variety of body contours.

Referring to FIG. 1, the structural assembly of an electrode 10 of the present invention includes several components operably connected to form the electrode. Namely, a connector, e.g., snap stud 12 and snap eyelet 22, operably attached to a skin fixation material layer 14 or platform. The electrode 10 further includes a retainer 16; a component/skin fixation material and barrier 18; a conductor 20 or conductive element; a drug containment matrix 24; a scrim-type material 26; and a release liner 28.

Figure 5A:
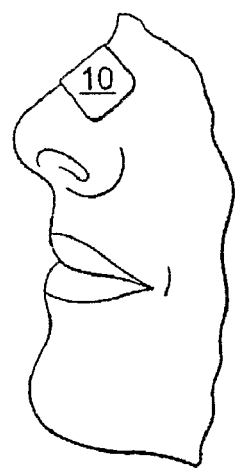
Figure 5B:
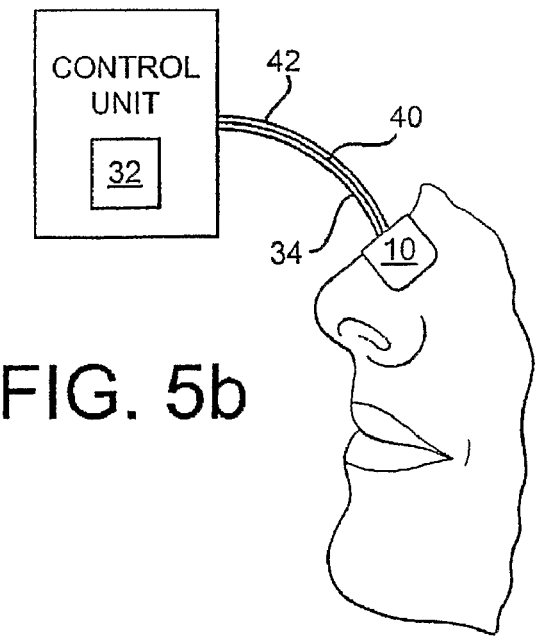

As desired, the electrode 10 may embody various geometric shapes related to its intended use. Some intended uses include, but are not limited to, placement on an appendage, nose, or ankle. FIGS. 5a and 5b depict one embodiment of the present invention wherein the electrode 10 is affixed to an individual's nose. The connector may be positioned in various locations and its placement should be carefully considered as its position may affect the time course and magnitude of electrical current flowing through the electrode 10. As can be seen in FIG. 1, the connector may be located near the center of the electrode. Conversely, the connector may be placed at a location that is not intended to be bent or formed.

The skin fixation material layer 14 or platform may be a water impermeable sheet including an adhesive for attaching to the skin, e.g., plastic tape. The skin fixation material 14 may cover the entire surface of the conductive element 20 and surrounding portions.

In another preferred embodiment of the present invention, the electrode 10 includes a platform 14, such as a base or substrate. The platform may include an adhesive for affixing to an individual's body. The retainer 16 is operably connected to the platform 14. A conductor 20 is operably connected to the platform 14 and is also electrically coupled to operate within the iontophoretic drug delivery system.

An iontophoretic drug delivery system generally refers to the components required to iontophoretically deliver a drug to an individual. While known iontophoretic drug delivery systems commonly include a power source and a dose controller within a common unit, e.g., a control unit; it is to be understood that the present invention is not to be limited as such. That is, various embodiments of the present invention include operable cooperation of the power source remote from the dose controller. As such, a dose controller 32 of the present invention is operably coupled to the conductor 20. A drug delivery matrix 24 is operably connected to the platform 14 and proximate the conductor 20, wherein the conductor, the drug delivery matrix, and the dose controller 32 cooperate to deliver a drug contained within the matrix to a user when the electrode 10 is affixed to the user and operably connected within the iontophoretic drug delivery system.

The retainer 16 may be fabricated from any pliant material capable of conforming to, or about, the contour of the body. Such pliable materials include, and are not limited to, plastics and soft metals. The shape of the retainer 16 can be in the form of a wire, film, or sheet. As such, the shape and material make-up of the retainer 16 provides it with a malleable characteristic that enables it to be shaped into a desired configuration and retained, i.e., structural memory.

In another embodiment of the present invention, the pliable retainer 16 is electrically conductive. As such, the conductive retainer 16 is integral with the conductor element 20. Accordingly, the electrode 10 may include a separate retainer 16 composed entirely of a pliable, conductive material; or, the electrode 10 may include an integral, pliable retainer and conductor. The integral conductor and retainer may comprise pliable and non-pliable segments.

The conductor 20 is preferably an active metal anode or cathode and can be composed of, for example, a conductive rubber, a resin film, a carbon film, or a metal foil such as Ag or Ag/AgCl. The conductor 20 may include a conventional current collector, such as a screen, mesh, or wire current collector fabricated from the same metal as that of the active anode; or, the conductor may be fabricated from other metals such as, but not limited to, brass coated with the same metal as the active anode or cathode metal.

Figure 2:
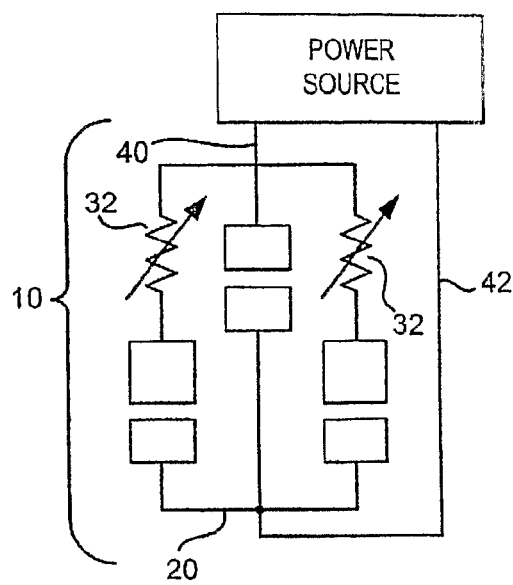
FIG. 2 is a block schematic diagram depicting one embodiment of the present invention.
Figure 3:
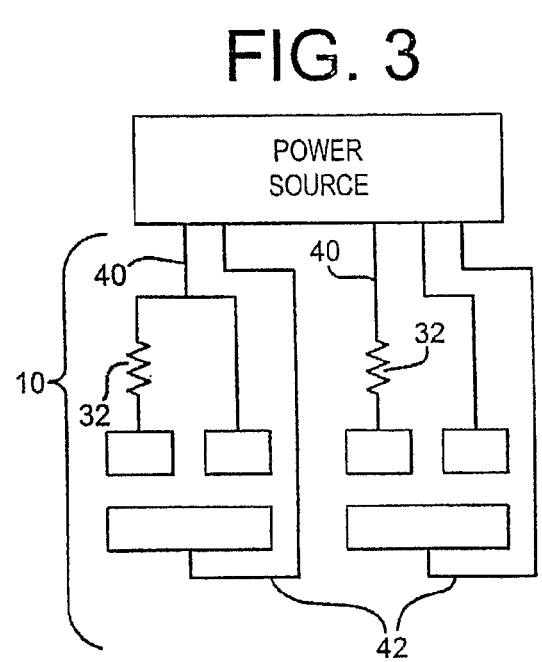
FIG. 3 is a block schematic diagram depicting one embodiment of the present invention.
Figure 4:
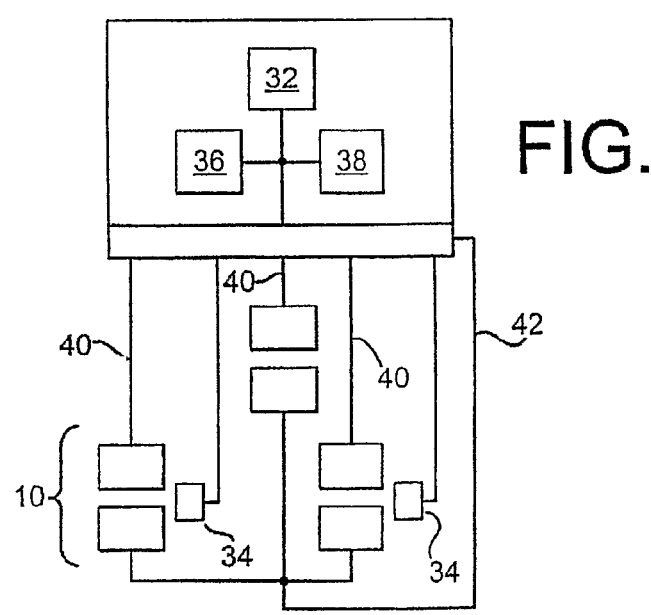
FIG. 4 is a block schematic diagram depicting one embodiment of the present invention; and, FIGS. 5a and 5b are perspective views of alternate embodiments of the present invention affixed to a nose.

Referring now to FIGS. 2-4, the electro-chemical reaction during iontophoresis requires a closed electrical circuit within the iontophoretic delivery system. Typically, a pair of conductors 20 is operably connected proximate to the treated area. The conductors 20 are generally designated as a drug delivery electrode 40 and a return 42, or dispersive, electrode.

More than one drug delivery electrode 40 and one dispersive electrode 42 can be utilized and numerous configurations include various ratios there between. That is, there may be one dispersive electrode 42 operably cooperating with more than one drug delivery electrode 40, and vice versa.

The drug delivery matrix 24 containing the medicament solution to be delivered may be composed of various materials—such as electrolytes, stability additives, preserving additives, pH regulating buffers, etc.—to facilitate retention of the medicament solution within the matrix. Additionally, the drug delivery matrix 24 may include a natural or synthetic amorphous member, a natural or synthetic sponge pad, a natural or synthetic lint free pad, and a natural or synthetic low particulate member. Indeed, numerous other configurations include: monolithic or layered viscoelastic solid hydrogels or liquid reservoirs contained with microporous membranes.

To further assist in maintaining the medicament within the drug delivery matrix 24, a scrim 26 may be positioned adjacent the drug delivery matrix. The scrim 26 is preferably fabricated of a natural or synthetic amorphous member, a natural or synthetic lint free pad, or a natural or synthetic low particulate member. The scrim 26 is not necessary and in some applications, the drug delivery matrix 24 can be exposed directly to the area to be treated.

The dose controller 32 is operably connected to the electrode 10 and may be contained within the electrode 10 or remotely housed within a portion of the iontophoretic drug delivery system. In the embodiments of the present invention shown in FIGS. 2 and 3, the dose controller 32 is a resistor operably connected to the electrode 10 and electrically coupled to either the drug 40 or return 42 electrodes. The resistor maybe fixed, variable, and/or adjustable.

In an alternate embodiment of the present invention shown in FIG. 4, the dose controller 32 is operably coupled to either the drug 40 and/or return 42 electrodes and housed within a portion of the iontophoretic delivery system. In this embodiment, the dose controller 32 includes a monitor 36 to observe an electrical characteristic—voltage, current, or resistance—associated with delivery of the drug. Also included is a sensor 34 operably coupled to the electrode(s) 40, 42 and proximate to the area being treated. Some examples of a sensor 34 capable of being utilized with the present invention, include, but are not limited to, a current shunt or a Hall Effect sensor. The sensor 34 is in signal communication with a monitor 36 and a current controller 38. Preferably, the sensor 34, monitor 36, and current controller 38 cooperate to monitor the amount of electrical current flowing through the conductor proximate to the area being treated. The electrical current can be programmable or adjusted manually. Furthermore, the electrical characteristics associated with delivery of the prescribed dosage can be adjusted in response to the monitored characteristics of the delivery.

Depending on the area to be treated and the desired uniformity or non-uniformity of the medical dose to be delivered, the electrode 10 can be constructed in various configurations. The power source can be contained on the electrode 10 itself, or the power source can be remotely located from the electrode and housed within a portion of the iontophoretic delivery system.

Some examples of conductor 20 and electrode 40, 42 configurations of the present invention include a single conductive element; a continuous, segmented, and/or conductive element; and a plurality of discrete conductive elements. The drug delivery matrix 24 is positioned proximate to the conductor 20 for operable cooperation there between and may be segmented accordingly. That is, the drug delivery matrix 24 may be continuous or segmented to cooperate with the conductor 20 to deliver the medicament to a prescribed area.

In FIG. 2, the drug delivery electrode 40 is operably coupled to a plurality of conductors. A pair of dose controllers 32, i.e., fixed and variable resistors, is operably coupled to separate drug matrices. Another drug delivery matrix is operably connected directly to the drug delivery electrode 40. A single return electrode 42 is operably coupled to the three drug matrices within the iontophoretic delivery system.

In FIG. 3, a pair of drug delivery electrodes 40 and return electrodes 42 are operably connected to separate drug delivery matrices. Each drug delivery electrode 40 is operably connected to its respective drug delivery matrix via a dose controller 32, i.e., resistor, and directly.

In FIG. 4, the dose controller 32 is not contained on the electrode itself, but rather remotely contained within a housing. In this embodiment, the dose controller is operably coupled to a monitor 36 and a current controller 38 that are also housed within a portion of the iontophoretic delivery system.

In all the embodiments of the present invention, the dose controller 32 is operably coupled to either, or both, of the drug delivery 40 electrode or the return 42 electrode to ensure proper delivery of the medicament. The predetermined dosage may require uniform or non-uniform delivery of the medicament. In addition, the area to be treated may include variations in skin and/or tissue resistance. As such, the dose controller 32 cooperates with the conductor 20 to take into account the electrical resistance so that the proper amount of medicament is delivered to the desired area(s). The dose controller 32 controls the level of electrical characteristic, e.g., current, associated with the conductor 20. As such, the electro-chemical reaction between the conductor 20 and the medicament retained within the drug delivery matrix 24 can be adjusted, i.e., increased, decreased, or maintained.

In embodiments of the present invention wherein a resistor is utilized as the dose controller 32 and is operably coupled to the conductor 20, more than one resistor can be utilized with the conductor 20. Depending on the circuit configuration, the amount of current (and voltage) directed to the treated area can be configured according to the areas to be treated and the amount of medicament to deliver. Furthermore, the dose controller 32 may be operably coupled to either the drug delivery 40 or dispersive 42 electrode. In addition, more than one dose controller 32 may be utilized with one or more conductors. In FIGS. 2-3, various resistors are shown in configuration with the conductors. Depending on the resistor's value, the amount of medicament will be delivered accordingly.

In FIG. 4, another embodiment of the present invention includes a current or voltage regulator utilized as the dose controller 32. The dose controller 32 is preferably housed within the iontophoretic delivery system and operably coupled to specific areas of the drug delivery matrix that pertain to the area(s) to be treated. In one such embodiment, a sensor 34 is operably coupled near the area to be treated. The electrical characteristics of the conductor associated with the treated area is monitored by the dose controller 32 and can be adjusted or maintained according to a prescribed amount of medicament to be delivered to the respective area.

Either embodiment of the dose controller disclosed above provides valuable benefits. For the resistor component, empirical data can be utilized so that the proper resistive value is utilized to ensure the prescribed amount of drug dosage to the area to be treated. Similarly, the feedback control embodiment utilizing a monitor and sensor provides the ability to adjust the electrical characteristics of the electrode such that various individuals will receive a more accurate amount of prescribed dosage despite the variety of resistance in an individual's skin tissue.

In an effort to further describe the present invention, an exemplification is now provided. It is to be understood that the present invention is not limited to this exemplification.

For iontophoretic applications to the nasal area, an electrode is selected that is capable of being properly affixed on or about the nose. When selecting an electrode for attachment to the nose, one may want to consider several features desired for the electrode, such as, but not limited to: size, shape, adhesive, number of drug delivery matrices, pattern of the drug delivery matrix, number of conductors, fixed or variable resistors, utilization of a feedback control system, malleable/bendable conductor(s), medicament and prescribed dose, etc. The selected electrode is then placed and molded to conform to the contour of the area to be treated. The bendable retainer conforms to the contours and retains its shape to facilitate its retention. The electrode can be operably connected to a power source before or after affixing the electrode to the treated area.

The entire area to be treated may be designated to receive a uniform drug dose or some areas may be specified to receive more or less medicament. The electrode includes a bendable retainer that is capable of being shaped and positioned about the nose so as to align the area(s) to be treated with the drug delivery matrix(ces). Due to the varying inherent resistance values in the nasal area, the operating electrical characteristics of each electrode are determined in view of the location and drug dose to be delivered through iontophoresis.

Such electrical design may utilize empirical data relating to the skin tissue resistance values on or about the nose. For an electrode incorporating fixed resistors, the value of each resistor is selected in response to the amount of electrical current desired to flow through the conductor and cooperate with the corresponding drug delivery matrix to ensure proper delivery. For an electrode incorporated with the feedback control system, the amount of current can be programmed with the dose controller. The sensor can monitor the amount of current wherein the current can be adjusted accordingly.

While specific embodiments of the present invention have been illustrated and described, numerous modifications come to mind without significantly departing from the spirit of the invention, and the scope of protection is only limited by the scope of the accompanying claims.

What is claimed is:

1. An electrode for an iontophoretic drug delivery system, the electrode comprising:
   a platform;
   a retainer including a malleable characteristic and being operably connected to the platform;
   a conductor being operably connected to the platform, the conductor further being electrically coupled within the iontophoretic drug delivery system;

a dose controller being operably coupled to the conductor; and, a drug delivery matrix being operably connected to the platform and proximate the conductor, wherein the conductor, the drug delivery matrix, and the dose controller cooperate to deliver a drug to a user when the electrode is affixed to the user and operably connected within the iontophoretic drug delivery system.

2. The electrode of claim 1 wherein the dose controller being housed within the iontophoretic drug delivery system and capable of monitoring and adjusting electrical current flowing within the conductor.

3. The electrode of claim 1 wherein the conductor comprises a plurality of discrete segments, each of the plurality of segments being proximate the drug delivery matrix.

4. The electrode of claim 3, wherein the dose controller being housed within the iontophoretic drug delivery system and capable of monitoring and adjusting electrical current flowing within the plurality of continuous segments of the conductor.

5. The electrode of claim 4, wherein the dose controller is electrically coupled to at least one of the plurality of segments of the conductor.

6. The electrode of claim 1, wherein the dose controller is housed within the iontophoretic drug delivery system and capable of monitoring and adjusting electrical current of at least one of the plurality of discrete segments of the conductor.

7. The electrode of claim 6 wherein the conductor comprises a plurality of discrete segments, each of the plurality of discrete segments being proximate the drug delivery matrix.

8. The electrode of claim 7, wherein the dose controller being electrically coupled to at least one of the plurality of discrete segments of the conductor.

9. The electrode of claim 1 further comprising:
a connector operably attached to the platform, the connector further being electrically coupled to the conductor.

10. The electrode of claim 1, further comprising:
an adhesive operably associated with the platform wherein the adhesive facilitates releasable securement of the electrode to the user.

11. The electrode of claim 1, wherein the dose controller is a resistor.

12. The electrode of claim 1, wherein the dose controller is a feedback circuit.

13. The electrode of claim 1, where the retainer is selected from the group of materials having structural memory.

14. The electrode of claim 1, wherein the conductor comprising:
an active conductor being electrically coupled within the iontophoretic drug delivery system; and,
a dispersive conductor being electrically coupled within the iontophoretic drug delivery system, wherein at least one of the pair of conductors including a malleable characteristic.

15. The electrode of claim 14 wherein the active or dispersive conductor comprises a plurality of discrete segments, each of the plurality of discrete segments being proximate one of the plurality of drug delivery areas.

16. The electrode of claim 15, wherein the dose controller being housed within the iontophoretic drug delivery system and capable of monitoring and adjusting electrical current flowing within the active or dispersive conductor.

17. The electrode of claim 16, wherein the dose controller being electrically coupled to at least one of the plurality of discrete segments and capable of monitoring and adjusting electrical current flowing within the active or dispersive conductor.

18. An electrode for an iontophoretic drug delivery system, the electrode comprising:
a platform;
a retainer including a malleable characteristic and being operably connected to the platform;
a conductor including a malleable characteristic and being operably connected to the platform; and,
a drug delivery matrix being operably connected to the platform and proximate the conductor,
wherein the conductor and the drug delivery matrix cooperate to deliver a drug to a user when the electrode is affixed to the user and operably connected within the iontophoretic drug delivery system.

19. The electrode of claim 18 further comprising:
a dose controller being operably coupled to the active conductor.

20. The electrode of claim 19 wherein the dose controller comprises a resistor.

21. The electrode of claim 19 wherein the dose controller is housed within the iontophoretic drug delivery system and is capable of monitoring and adjusting electrical current flowing within the active conductor.

22. The electrode of claim 18 wherein the conductor comprises a plurality of continuous segments, each of the plurality of continuous segments positioned proximate the drug delivery matrix.

23. The electrode of claim 22, wherein the dose controller is housed within the iontophoretic drug delivery system and is capable of monitoring and adjusting electrical current flowing within the plurality of continuous segments of the conductor.

24. The electrode of claim 23, wherein the dose controller is electrically coupled to at least one of the plurality of continuous segments of the conductor.

25. The electrode of claim 18 wherein the conductor comprises a plurality of discrete segments, each of the plurality of discrete segments positioned proximate the drug delivery matrix.

26. The electrode of claim 25, wherein the dose controller is housed within the iontophoretic drug delivery system and is capable of monitoring and adjusting electrical current flowing within the plurality of discrete segments of the active conductor.

27. The electrode of claim 25, wherein the dose controller is electrically coupled to at least one of the plurality of discrete segments of the active conductor.

28. The electrode of claim 18 further comprising:
a connector being operably attached to the platform, the connector further being electrically coupled to the conductor.

29. For an iontophoretic drug delivery system capable of delivering a medicament to a bodily area having a tissue resistance, the system including a dose controller and an electrode, the electrode comprising a malleable retainer, a conductor, and a drug delivery matrix capable of containing the medicament wherein the conductor is operably coupled to the dose controller and operably connected within the drug delivery matrix, a method comprising the steps of:
selecting an electrical characteristic for the dose controller in response to the corresponding tissue resistance of the bodily area;
placing the electrode proximate the bodily area;
aligning the drug delivery matrix proximate the bodily area; and, conforming the malleable retainer to the bodily area,
wherein the medicament is administered to the bodily area in response to activation of the iontophoretic drug delivery system and the electrochemical cooperation between the conductor, dose controller, and the drug delivery matrix.

30. The method of claim 29 wherein the dose controller is a resistor.

31. The method of claim 30 wherein the resistor is fixed.

32. The method of claim 30 wherein the resistor is variable.

33. The method of claim 29 wherein the dose controller comprises a sensor and a monitor.

34. The method of claim 29 further comprising:
setting an amount of electrical current supplied to the conductor; and,
sensing the electrical current in the conductor.

35. The method of claim 34 further comprising:
adjusting the amount of electrical current supplied to the conductor in response to tissue resistance of the area.

36. The method of claim 29 wherein the conductor is integral with the malleable retainer.

37. In electrode for an iontophoretic drug delivery system, the electrode comprising:
a platform;
a conductor being operably connected to the platform, the conductor further being electrically coupled within the iontophoretic drug delivery system;
a retainer including a malleable characteristic and being integral with the conductor;
a dose controller being operably coupled to the conductor; and,
a drug delivery matrix being operably connected to the platform and proximate the conductor,
wherein the conductor, the drug delivery matrix, and the dose controller cooperate to deliver a drug to a user when the electrode is affixed to the user and operably connected within the iontophoretic drug delivery system.

38. The electrode of claim 37 wherein the dose controller being housed within the iontophoretic drug delivery system and capable of monitoring and adjusting electrical current flowing within the conductor.

39. The electrode of claim 37 wherein the conductor comprises a plurality of discrete segments, each of the plurality of segments being proximate the drug delivery matrix.

40. The electrode of claim 39, wherein the dose controller being housed within the iontophoretic drug delivery system and capable of monitoring and adjusting electrical current flowing within the plurality of continuous segments of the conductor.

41. The electrode of claim 40, wherein the dose controller is electrically coupled to at least one of the plurality of segments of the conductor.

42. The electrode of claim 37, wherein the dose controller is housed within the iontophoretic drug delivery system and capable of monitoring and adjusting electrical current of at least one of the plurality of discrete segments of the conductor.

43. The electrode of claim 42 wherein the conductor comprises a plurality of discrete segments, each of the plurality of discrete segments being proximate the drug delivery matrix.

44. The electrode of claim 43, wherein the dose controller being electrically coupled to at least one of the plurality of discrete segments of the conductor.

45. The electrode of claim 37 further comprising:
a connector operably attached to the platform, the connector further being electrically coupled to the conductor.

46. The electrode of claim 37, further comprising:
an adhesive operably associated with the platform wherein the adhesive facilitates releasable securement of the electrode to the user.

47. The electrode of claim 37, wherein the dose controller is a resistor.

48. The electrode of claim 47, wherein the dose controller is a feedback circuit.

* * * * *